United States Patent
Fugoso et al.

[11] Patent Number: 5,961,510
[45] Date of Patent: Oct. 5, 1999

[54] FLEXIBLE CATHETER

[75] Inventors: Mauricio L. Fugoso, Chula Vista; Karen M. Rowean, San Diego; Michelle E. Siebold, Carlsbad, all of Calif.

[73] Assignee: Medtronic, Inc., Minneapolis, Minn.

[21] Appl. No.: 08/938,045

[22] Filed: Sep. 26, 1997

[51] Int. Cl.⁶ .................................................. A61M 25/00
[52] U.S. Cl. .......................................... 604/524; 604/526
[58] Field of Search .................................. 604/523, 524, 604/264, 96, 526; 600/435

[56] References Cited

U.S. PATENT DOCUMENTS

| | | | |
|---|---|---|---|
| 4,960,410 | 10/1990 | Pinchuk | 604/96 |
| 5,328,472 | 7/1994 | Steinke et al. | 604/102 |
| 5,410,797 | 5/1995 | Steinke et al. | 29/435 |
| 5,454,795 | 10/1995 | Samson | 604/282 |
| 5,460,608 | 10/1995 | Lodin et al. | 604/96 |
| 5,599,326 | 2/1997 | Carter | 604/282 |
| 5,690,613 | 11/1997 | Verbeek | 604/103 |
| 5,702,373 | 12/1997 | Samson | 604/280 X |

*Primary Examiner*—Corrine McDermott
*Assistant Examiner*—A T Nguyen
*Attorney, Agent, or Firm*—Dianne Plunkett Latham; Harold R. Patton

[57] ABSTRACT

A medical catheter comprising a distal shaft having a greater flexibility than the proximal shaft. The proximal shaft has a helical end portion of reduced outer diameter which is integral with and extending from the distal end of the proximal shaft. The helical end portion slidingly fits within a portion of the proximal end of the distal shaft. The helical end portion is bonded to at least a portion of the distal shaft to form a fluid-tight seal. The pitch of the helical end portion may be constant or variable. The helical turns may be abutting or spaced apart. A guidewire shaft centrally extends longitudinally through the proximal and distal shaft such that fluid can be transmitted through the proximal and distal shaft, exterior to the guidewire shaft.

21 Claims, 3 Drawing Sheets

FLEXIBLE CATHETER

FIELD OF THE INVENTION

The present invention relates to a catheter of constant outer diameter having a flexible, non-kinking shaft and more particularly to a catheter having a flexible distal shaft portion and a stiffer proximal shaft portion.

BACKGROUND OF THE INVENTION

Percutaneous transluminal coronary angioplasty (PTCA) is used to increase the lumen diameter of a coronary artery partially or totally obstructed by a build-up of cholesterol fats or atherosclerotic plaque. Typically a first guidewire of about 0.038 inches in diameter is steered-through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen. The dilatation of the occlusion, however, can form flaps, fissures and dissections which threaten reclosure of the dilated vessel or even perforations in the vessel wall.

Although the dimensions in the above example are suited to the coronary arteries, any body lumen can be treated by percutaneous transluminal angioplasty (PTA), including the vas deferens, ducts of the gallbladder, prostate gland, trachea, bronchus and liver. The body lumens range in diameter from small coronary vessels of 3 mm or less to 28 mm in the aortic vessel. The invention applies to acute and chronic closure or reclosure of body lumens.

It is advantageous for catheter shafts to have a stiff proximal end for pushability and a more flexible distal end for better tracking through tortuous lesions. Abutting stiff tubular materials to more flexible tubular materials results in a point at which kinking can occur. What is needed is a transition area therebetween to provide a smooth transition between the stiff proximal section and the more flexible section of the catheter shaft and thereby reduce kinking.

U.S. Pat. No. 4,960,410 to Pinchuk for "Flexible Tubular Member for Catheter Construction" discloses a spirally cut tubular member which extends through the balloon to the distal end of the catheter. The tubular member includes a first relatively stiff tube that is spirally cut along a distal portion and also includes a second more flexible tube that covers the spirally cut distal portion of the stiff tube to make a distal portion of the tubular member more flexible than a proximal portion of the elongated tubular member.

U.S. Pat. No. 5,599,326 to Carter for "Catheter with Multi-Layer Section" discloses an interior stiffener comprising a spirally cut tube member and an exterior tube member.

SUMMARY OF THE INVENTION

It is an object of the invention to provide a smooth, flexible and kink-resistant transition between the catheter shaft stiff proximal end and the more flexible distal end while retaining a uniform outer diameter between the proximal shaft portion and the distal shaft portion. The present invention is accomplished by providing an apparatus comprising a distal shaft having a greater flexibility than the proximal shaft. The proximal shaft has a helical end portion of reduced outer diameter which is integral with and extending from the distal end of the proximal shaft. The helical end portion slidingly fits within a portion of the proximal end of the distal shaft. The helical end portion is bonded to at least a portion of the distal shaft to form a fluid-tight seal. The pitch of the helical end portion may be constant or variable. The helical turns may be abutting or spaced apart. A guidewire shaft centrally extends longitudinally through the proximal and distal shaft such that fluid can be transmitted through the proximal and distal shaft, exterior to the guidewire shaft.

DETAILED DESCRIPTION OF THE PREFERRED EMBODIMENTS

Figure 1:
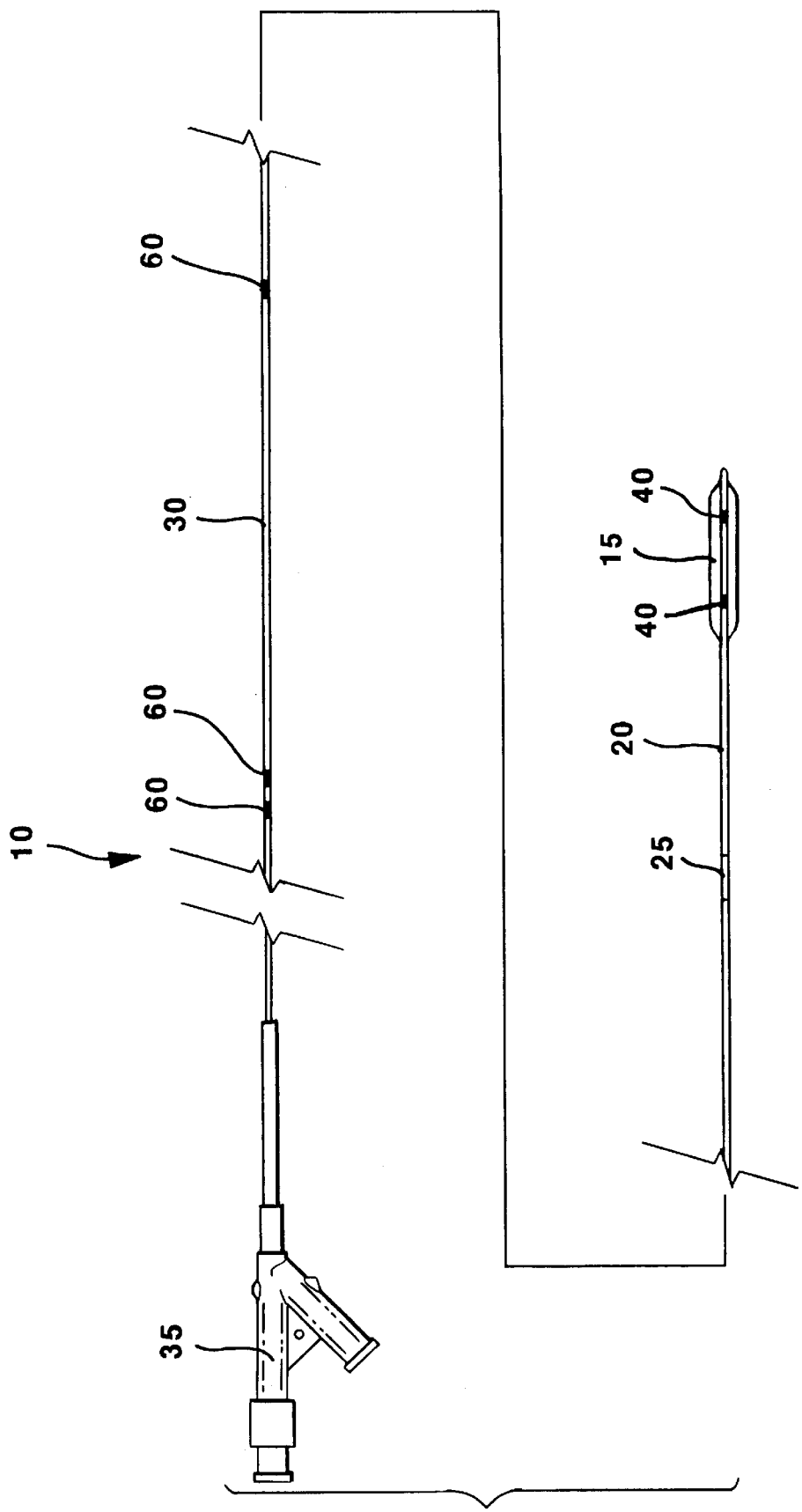
FIG. 1 is a plan view of the catheter of the invention.
Figure 2:
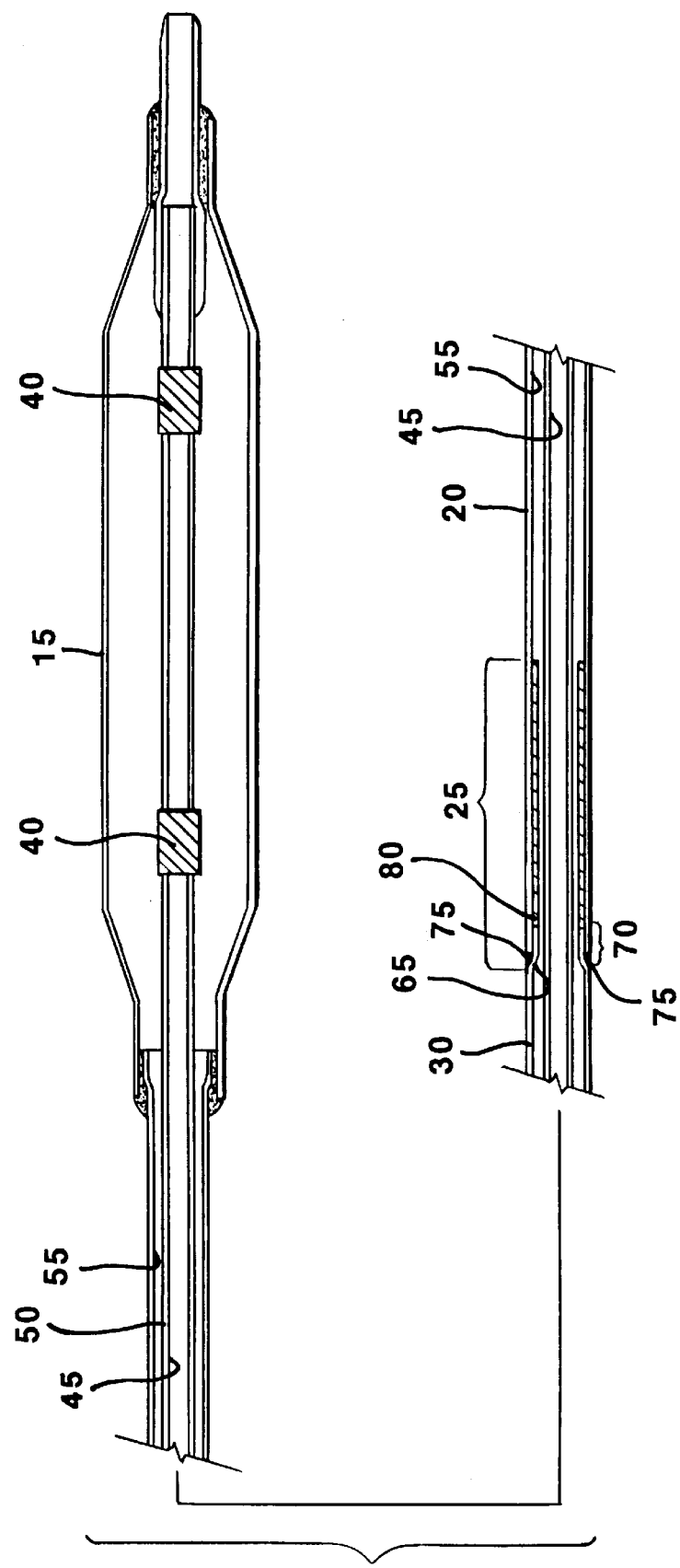
FIG. 2 is a cross-section of the distal end of the catheter of FIG. 1.
Figure 3:
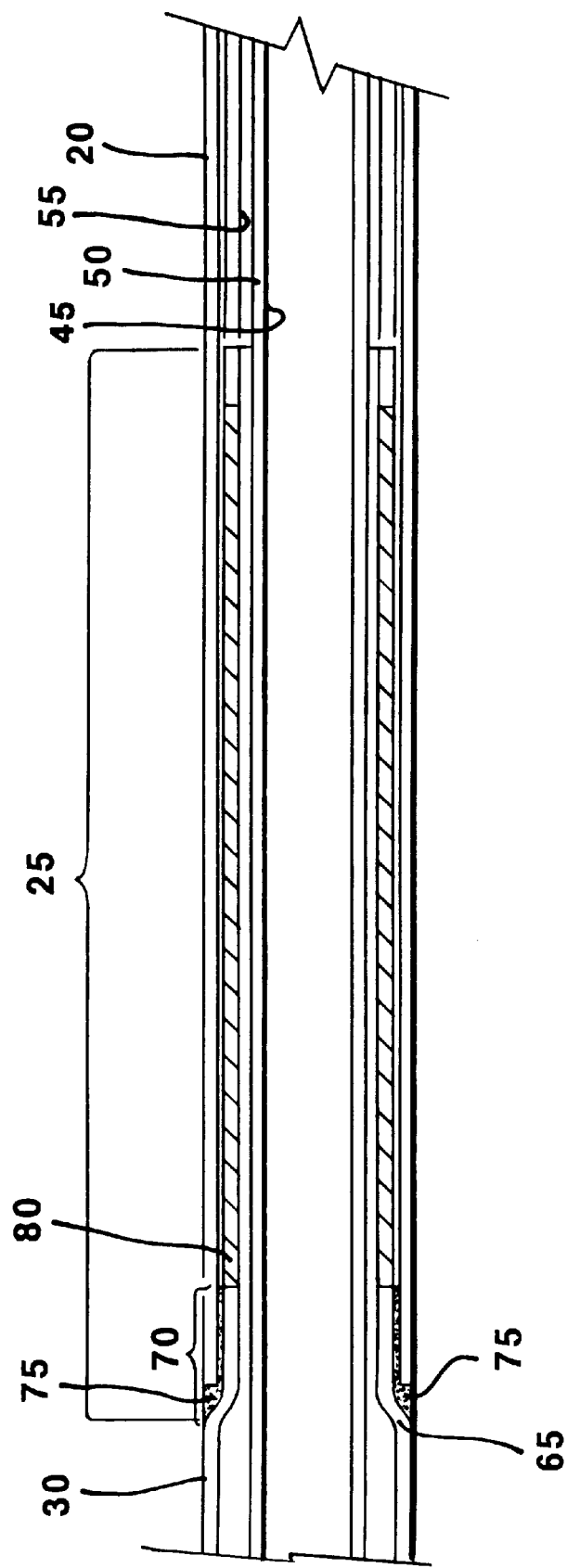
FIG. 3 is a cross-section of the transition section of the catheter of FIG. 2.

Referring to FIG. 1, Applicant's catheter 10 is comprised of a balloon 15, distal shaft 20, transition 25, proximal shaft 30 and manifold 35. The spirally cut transition 25 is designed to provide a smooth transition between the stiff proximal shaft 30 and the more flexible distal shaft 20. This reduces kinking and prevents guidewire lockup or damage, especially during backloading the guidewire into the catheter. In instances where the catheter is deep into the guide catheter, the flexible transition allows the catheter to bend with the bends in the guide catheter instead of butting against the wall of the guide catheter, thus increasing the trackability of the distal section which is out in the torturous vessel. A conventional over-the-wire design consists of a guidewire shaft 50 which defines a guidewire lumen 45 running the length of the catheter 10. The guidewire shaft 50 is coaxially disposed within the proximal shaft 30. The inner diameter and the outer diameter of the distal end of the proximal shaft 30 is necked down at 65. The transition 25 beginning at the neck 65 and ending at the distal end of the proximal shaft 30 is approximately 1 inch (2.54 cm) long. The outer diameter of the proximal shaft 30 before necking is approximately 0.041 inches (1.04 mm). After necking 65, the outer diameter of the proximal shaft 30 is greater than 0.0315 inches (0.800 mm), preferably 0.034 inches (0.86 mm) which will yield optimum in/deflation times. The inner diameter of the proximal shaft 30 after necking down is approximately 0.029 inches (0.737 mm).

The distal end of the proximal shaft 30 is spirally cut into a coil to define the transition 25. A constant pitch of 24 degrees with 2 coils per mm is preferred. Other pitches or variable pitches may be preferred in certain alternate applications. Smaller angles lead to less flexibility due to more coils per the specified distance and vice versa. An example of this would be using this type of transition in place of a strain relief at the proximal end of the catheter next to the manifold. In this application, fewer coils per the specified distance would be more desirable. The more distal you move down the catheter toward the balloon, the more coils per the specified distance, thus the more flexible the transition. To create the spiral cut, a 0.0280 inch mandrel is inserted into the distal end of the proximal shaft 30 which is then cut using any conventional means such as a razor blade maintained at a fixed angle to the cutting surface. This can be done manually with a fixture maintaining the razor at a fixed angle while the catheter section is rotated using a motorized device with a mounting chuck. The operator holds the razor blade manually against the cutting surface. An alternate to this method could be that the razor blade is held within a fixture that provides the pressure required to enable the cutting. The distal end of the proximal shaft 30 should be trimmed to within 1 mm–2 mm from the last distal coil. The coils should be cut all the way through. The length of the proximal shaft 30 between the neck 65 and the first proximal spiral 80 should be about 0.118 inches (3 mm). The length of the spiraled area should be about 0.748 inches (19 mm). For optimum tracking, flexibility, and kink resistance, transition 25 is preferably not less than about ¾ inches. The length of transition 25 could vary depending on where along the catheter it is placed. The length between the last distal spiral 80 and the distal end of the proximal shaft 30 is preferably about 0.059 inches (1.50 mm). The length from the neck 65 to the distal end of the distal shaft 20 is about 11.81 inches (300.0 mm). The spirally cut transition 25 is designed to provide a smooth transition between the stiff proximal shaft 30 and the more flexible distal shaft 20. Having a more gradual stiffness gradient reduces kinking and increases flexibility for better tracking. Transition section 25 is located on the catheter shaft in such a position to be compatible with the guide catheter. Guiding catheters often have preset curves at the distal end or segments of differing flexibility. The transition 25 on a catheter such as a balloon catheter 10 should be aligned with the preset curve or a segment of suitable flexibility so that an advantageous length of the balloon catheter protrudes from the guiding catheter into the vessel. The transition 25 is placed such that it is far enough back on the balloon catheter 10 so that the most flexible portion of the balloon catheter 10 resides in the vessel. In instances where the catheter is very deep into the guiding catheter, the flexible transition is advantageous in that it allows the catheter 10 to track the bends in the guiding catheter, thus improving the tracking of the distal portion in the vessel and not kinking at that point.

The outer diameter of the distal shaft 20 is approximately 0.041 inches (1.04 mm) over the transition section 25. The proximal end of the distal shaft 20 is coaxially slid over the distal end of the proximal shaft 30 to within about 0.5 mm of the neck 65, while the assembly is still on the 0.0280 inch mandrel. The proximal end of the distal shaft 20 is bonded at the neck 65 of the proximal shaft 30 using any conventional means such as adhesive 75, heat bonding or welding. The preferred means is to place a drop of U.V. adhesive, as for example #3311 Loctite® (manufactured by Loctite Corp. in Hartford Conn.) into the gap, wick it under the distal shaft 20, slide the proximal end of the distal shaft 20 up to the neck 65 then cure the adhesive while rotating the parts. Form a bond 70 which is about 1 mm long. The adhesive should not extend beyond the second spiral 80. After bonding, the 0.0280 inch mandrel is removed.

The proximal shaft 30 may be formed of a stiff material such as polyimide. Other materials which would be suitable for the necessary pushability include PEEK. Those skilled in the art would recognize that any material which has high column strength in a thin walled configuration of the appropriate size would be suitable. The distal shaft 20 may be formed of a more flexible material such as Polyethylene (PE) or Nylon. The proximal shaft 30 may have several visual Marker Bands 60 to indicate the various approaches, as for example, the brachial approach. The distal end of the proximal shaft's material could be heat laminated to the more flexible material of the distal shaft 20 proximal end.

The distal shaft 20 may be optionally necked down to improve tracking at a point distal to the transition 25. The outer diameter of the distal shaft 20 before necking is approximately 0.041 inches (1.04 mm). The distal shaft 20 is necked down to a first neck with an outer diameter of approximately 0.038 inches which is approximately 0.5 inches from the distal end of the transition 25. The distance between neck-down 65 and the first neck of the distal shaft 20 is 1.5 inches. The distal shaft 20 is necked down again into a second neck distal to the first neck to an outer diameter of approximately 0.034 inches beginning approximately 5 inches proximal of the distal end of the balloon 15. The distal shaft 20 first and second neck produce better tracking. The first and second neck downs in the distal shaft 20 are sized to maximize tracking vs. inflation/deflation time. The distance between neck-down 65 and the proximal end of balloon 15 is 11.81 inches.

The guidewire shaft 50 is made of High Density Polyethylene (HDPE). It has an inner diameter of 0.017 inches (0.43 mm) suitable for passing standard 0.014 inch guidewires. Those skilled in the art would recognize that the dimension varies depending on the application and the size of device being passed. The outer diameter of the guidewire shaft 50 is 0.023 inches.

For the Balloon 15 any conventional material may be used such as Nylon, polyethylene (PE) or polyethylene terephthalate (PET). The balloon typically has one or more marker bands 40 made of a material such as platinum/iridium for visualization under fluoroscopy. Those skilled in the art would recognize that any conventional balloon design would be suitable. The proximal end of the balloon 15 is affixed to the distal end of the distal shaft 20. The distal end of the distal shaft 20 can be flared larger to accommodate bonding of the balloon 15 to the distal end of the distal shaft. The balloon 15 is in fluid communication with the inflation lumen 55.

Whereas Applicant's invention depicts a shaft transition for an over-the-wire coronary catheter those skilled in the art would recognize that such a transition could be used for any catheter including rapid exchange or fixed wire catheters and other applications such as peripheral etc. The preceding specific embodiments are illustrative of the practice of the invention. It is to be understood, however, that other expedients known to those skilled in the art or disclosed herein, may be employed without departing from the scope of the appended claims.

| No. | Component |
|-----|-----------|
| 10 | Catheter |
| 15 | Balloon |
| 20 | Distal Shaft |
| 25 | Transition Section |
| 30 | Proximal Shaft |
| 35 | Manifold |
| 40 | Balloon Marker Bands |
| 45 | Guidewire Lumen |
| 50 | Guidewire Shaft |
| 55 | Inflation Lumen |
| 60 | Shaft Visual Marker Bands |
| 65 | Neck-Down |
| 70 | Bond |
| 75 | Adhesive |
| 80 | Spiral |

What is claimed is:

1. A medical catheter comprising:

a proximal section having a proximal end and a distal end;

a transition section having a proximal end and a distal end;

a distal section having a proximal end and a distal end;

a balloon having a proximal end and a distal end, the distal end of the proximal section forming the transition section, the distal end of the transition section being coaxially affixed to and covered by the proximal end of the distal section, the distal end of the distal section being affixed to the proximal end of the balloon;

a guidewire shaft defining a guidewire lumen, the guidewire shaft extending longitudinally and coaxially throughout the proximal section, the transition section, the distal section and the balloon with enough clearance between an outer diameter of the guidewire shaft and an inner diameter of the proximal section, transition section, distal section and balloon so as to define an inflation lumen therebetween and maintain fluid communication with the balloon; and the transition section further comprising a necked-down area of reduced outer diameter beginning at the proximal end of the transition section, the area of reduced outer diameter having a spirally cut distal portion to increase flexibility and kink resistance, the distal end of the transition section ending proximal to the proximal end of the balloon.

2. The catheter according to claim 1 wherein the distal section is more flexible than the proximal section and the transition section is of intermediate flexibility to the proximal section and to the distal section.

3. The catheter according of claim 1 wherein the spiral cut extends completely through the thickness of the transition section.

4. The catheter of claim 1 wherein the spiral cut is at a constant pitch.

5. The catheter of claim 4 wherein the pitch is at 24 degrees with two spiral coils per mm.

6. The catheter of claim 1 wherein the spiral cut is at a variable pitch.

7. The catheter according of claim 1 wherein the spiral cut is continuous.

8. The catheter according of claim 1 wherein the proximal section is made of polyimide.

9. The catheter according of claim 1 wherein the distal section comprises a material selected from polyethylene and nylon.

10. The catheter according of claim 1 wherein the guidewire shaft is made of high density polyethylene.

11. The catheter according of claim 1 wherein the length of the spirally cut portion is not less than 19 mm (0.748 inches).

12. A medical catheter comprising:
a proximal shaft having an outer diameter;
a distal shaft having greater flexibility than the proximal shaft, a proximal portion of the proximal shaft having an outer diameter that is substantially the same as the outer diameter of the distal shaft, the proximal shaft further comprising:
a helical end portion of reduced outer diameter integral with and extending from a distal end of the proximal shaft, the helical end portion slidingly fitting within a portion of a proximal end of the distal shaft; and
the helical end portion being bonded to the distal shaft over at least a proximal portion of the helical end portion to form a fluid-tight seal.

13. The catheter according to claim 12 wherein the helical end portion is formed from a reduced diameter portion of the proximal shaft.

14. The catheter according to claim 12 wherein the helical portion has a constant pitch.

15. The catheter according to claim 12 wherein the helical portion has a variable pitch.

16. The catheter according to claim 15 wherein the helical portion has a pitch which is greater at a distal end than at a proximal end.

17. The catheter according to claim 12 wherein the helical portion is defined by one or more turns and wherein at least a portion of the turns of the helical portion are in abutting relation.

18. The catheter according to claim 12 wherein at least a portion of the turns of the helical portion are spaced apart.

19. The catheter according to claim 12 also comprising a tube extending longitudinally within the proximal shaft and the distal shaft such that a fluid can be transmitted through the proximal shaft and the distal shaft exterior to the centrally extending tube.

20. The catheter according to claim 12 also comprising a balloon affixed to the distal shaft, the balloon being in fluid communication with the proximal shaft.

21. The catheter of claim 19 wherein the centrally extending tube is adapted to receive a guidewire.

* * * * *